US007687072B2

(12) United States Patent
Worley et al.

(10) Patent No.: US 7,687,072 B2
(45) Date of Patent: *Mar. 30, 2010

(54) BIOCIDAL PARTICLES OF METHYLATED POLYSTYRENE

(75) Inventors: Shelby D. Worley, Auburn, AL (US); Yongjun Chen, Auburn, AL (US)

(73) Assignee: Auburn University, Auburn, AL (US)

( * ) Notice: Subject to any disclaimer, the term of this patent is extended or adjusted under 35 U.S.C. 154(b) by 855 days.

This patent is subject to a terminal disclaimer.

(21) Appl. No.: 10/287,449

(22) Filed: Oct. 31, 2002

(65) Prior Publication Data

US 2004/0086480 A1    May 6, 2004

(51) Int. Cl.
A61K 9/14    (2006.01)
(52) U.S. Cl. .................. 424/489; 424/400; 514/772.1
(58) Field of Classification Search .............. None
See application file for complete search history.

(56) References Cited

U.S. PATENT DOCUMENTS

| 2,225,384 | A | | 12/1940 | Graenacher et al. |
| 3,519,608 | A | | 7/1970 | Kelley et al. |
| 3,931,213 | A | | 1/1976 | Kaminski et al. |
| 4,000,293 | A | | 12/1976 | Kaminski et al. |
| 4,012,565 | A | * | 3/1977 | Freedman et al. ........... 523/127 |
| 4,349,646 | A | | 9/1982 | Nudel et al. |
| 4,420,590 | A | | 12/1983 | Gartner |
| 4,478,984 | A | * | 10/1984 | Bryan ................. 525/333.6 |
| 4,589,984 | A | * | 5/1986 | Legrand et al. ............. 210/522 |
| 4,681,948 | A | | 7/1987 | Worley |
| 4,767,542 | A | | 8/1988 | Worley |
| 4,826,924 | A | | 5/1989 | Kourai |
| 4,842,932 | A | | 6/1989 | Burton |
| 4,955,392 | A | | 9/1990 | Sorkin |
| 5,057,612 | A | | 10/1991 | Worley et al. |
| 5,126,057 | A | | 6/1992 | Worley et al. |
| 5,284,157 | A | | 2/1994 | Miller et al. |
| 5,338,859 | A | | 8/1994 | Bhattacharya |
| 5,490,983 | A | | 2/1996 | Worley et al. |
| 5,561,183 | A | | 10/1996 | Kwon et al. |
| 5,670,646 | A | | 9/1997 | Worley et al. |
| 5,683,709 | A | * | 11/1997 | Yamada et al. ............. 424/409 |
| 5,756,764 | A | | 5/1998 | Fenteany et al. |
| 5,785,963 | A | | 7/1998 | Tseng |
| 5,882,357 | A | | 3/1999 | Sun et al. |
| 5,889,130 | A | | 3/1999 | Worley et al. |
| 5,902,818 | A | | 5/1999 | Worley et al. |
| 5,968,599 | A | | 10/1999 | Jung et al. |
| 5,981,668 | A | | 11/1999 | Fujita et al. |
| 6,294,185 | B1 | | 9/2001 | Worley |
| 6,823,530 | B2 | | 11/2004 | Quincy, III |
| 2003/0143187 | A1 | | 7/2003 | Worley |

FOREIGN PATENT DOCUMENTS

EP    0 047 050 A1    3/1982

| EP | 0 047 050 B1 | 3/1982 |
| JP | 2000-79159 A | 3/2000 |
| WO | WO 94/20118 A1 | 9/1994 |
| WO | WO 01/07709 A1 | 2/2001 |
| WO | WO 02/06579 A2 | 1/2002 |
| WO | WO 02/30477 A1 | 4/2002 |

OTHER PUBLICATIONS

Odian "Principles of Polymerization"1991, pp. 510-512.*
Odian, "Principles of Polymerization" 1991.*
Merkle disclosure, 1993.*
Svec et al., 273 Science 205 (1996).*
Sun, Y., and Gang Sun, "Durable and Refreshable Polymeric N-Halamine Biocides Containing 3-(4'-vinylbenzyl)-5,5-dimethylhydantoin," *Journal of Polymer Science: Part A: Polymer Chemistry* 39:3348-3355, 2001.
Sun, Y., and Gang Sun, "Synthesis, Characterization, and Antibacterial Activities of Novel N-Halamine Polymer Beads Prepared by Suspension Copolymerization," *Macromolecules* 35:8909-8912, 2002.
Asinger, F., et al., "Zur Darstellung von Imidazolidin-Thionen-(4) und Imidazolin-(3)-Thionen-(5)," *Mh. Chem.* 98:338-352, 1967.
Asinger, F., et al., "Zur Kenntnis der Hydrolyse Substituierter Imidazolidin-Thion-(4)," *Mh. Chem* 98:1843-1851, 1967.
Bellar, T.A., et al., "The Occurrence of Organohalides in Chlorinated Drinking Waters," *J. Am. Waters Works Assoc.* 66:703-706, 1974.
Buchenska, J., "Polyamide Fibers (PA6) With Antibacterial Properties," *J. Applied Polymer Sci.* 61: 567-576, 1996.
Chemical Abstract No. 40044, 1968.
Chemical Abstract No. 444909, 1970.
Cho, W.J., et al., "Synthesis and Biocidal Activities of Polymer. II. Bactericidal Activity of Homopolymer of AcDP and Copolymer of AcD With MMA," *J. Macromolecular Sci.—Pure and Applied Chem.* 32(3):479-495, 1995.
Christian, J.D., "4-Imidazolidinethiones," *J. Org. Chem.* 22:396-399, 1957.
DuPont Advertisement, *Chem. Eng. News* 26(6), 1948.
Elrod, D.B., et al., "A Facile Synthetic Approach to Imidazolidinone Biocides," *Ind. Eng. Chem. Res.* 38(11):4144-4149, 1999.
Emerson, D.W., et al., "Functionally Modified Poly(styrene-Divinylbenzene). Preparation, Characterization, and Bactericidal Action," *Ind. & Eng. Chem. Prod. Res. and Dev.* 17(3):269-274, 1978.
Emerson, D.W., "Polymer-Bound Active Chlorine: Disinfection of Water in a Flow System. Polymer Supported Reagents. 5," *Ind. & Eng. Chem. Res.* 29(3):448-450, 1990.

(Continued)

Primary Examiner—Eric E Silverman
(74) Attorney, Agent, or Firm—Christensen O'Connor Johnson Kindness PLLC

(57) ABSTRACT

Methylated polystyrene having pendant N-halamine and N-halamine precursor groups. Biocidal particles have been prepared by reacting highly crosslinked methylated polystyrene beads as starting materials with various N-halamine precursor compounds. The resulting polymer beads are halogenated with chlorine or bromine. The porous beads will be useful in disinfection applications, as well as for sanitization and controlling noxious odor when mixed with absorbent materials in items such as disposable diapers, infant swimwear, incontinence pads, bandages, sanitary napkins, pantiliners, mattress covers, shoe inserts, sponges, animal litter, carpets, and fabrics.

21 Claims, No Drawings

OTHER PUBLICATIONS

Emerson, D.W., "Slow Release of Active Chlorine and Bromine From Styrene-Divinylbenzene Copolymers Bearing N,N-Dichlorosulfonamide, N-Chloro-N-Alkylsulfonamide, and N-Bromo-N-Alkylsulfonamide Functional Groups. Polymer-Supported Reagents. 6," *Ind. & Eng. Chem. Res.* 30(11):2426-2430, 1991.

Hayes, R.A., "Polymeric Chain Transfer Reactions. Polymerization of Some Vinyl Monomers in the Presence of Vinyl Polymers," *J. Polymer Sci. XI*(6):531-537, 1953.

Hazziza-Laskar, J., et al., "Biocidal Polymers Active by Contact. I. Synthesis of Polybutadiene With Pendant Quaternary Ammonium Groups," *J. App. Polymer Sci.* 50(4):651-662, 1993.

Hazziza-Laskar, J., et al., "Biocidal Polymers Active by Contact. IV. Polyurethanes Based on Polysiloxanes With Pendant Primary Alcohols and Quaternary Ammonium Groups," *J. App. Polymer Sci.* 58(1):77-84, 1995.

Hoff, J.C., et al., "Comparison of the Biocidal Efficiency of Alternative Disinfectants," *J. Am. Water Works. Assoc.* 73:40-44, 1981.

Kanazawa, A., et al., "Polymeric Phosphonium Salts as a Novel Class of Cationic Biocides. III. Immobilization of Phosphonium Salts by Surface Photografting and Antibacterial Activity of the Surface-Treated Polymer Films," *J. Polymer Sci.* 31(6):1467-1472, 1993, Part A: Polymer Chemistry.

Kanazawa, A., et al., "Polymeric Phosphonium Salts as a Novel Class of Cationic Biocides. VI. Antibacterial Activity of Fibers Surface-Treated With Phosphonium Salts Containing Trimethoxysilane Groups," *J. App. Polymer Sci.* 52:641-647, 1994.

Kawata, T., et al., "First Permanently Antibacterial and Deodorant Fibers," *Chem. Fibers International* 48:38-43, 1998.

Kreft, P., et al., "Converting From Chlorine to Chloramines: A Case Study," *J. Am. Water Works Assoc.* 77:38-45, 1985.

Mintz, M.J., et al., "τ-Butyl Hypochlorite," *Org. Syntheses., Coll.* 5:184-187, 1969. [corrected from 1963 to 1969].

Norman, T.S., et al., "The Use of Chloramines to Prevent Trihalomethane Formation," *J. Am. Water Works Assoc.* 72:176-180, 1980.

Nurdin, N., et al. "Biocidal Polymers Active by Contact. III. Aging of Biocidal Polyurethane Coatings in Water," *J. Applied Polymer Sci.* 50:671-678, 1993.

Nurdin, N., et al., "Biocidal Polymers Active by Contact. II. Biological Evaluation of Polyurethane Coatings With Pendant Quaternary Ammonium Salts," *J. App. Polymer Sci.* 50:663-670, 1993.

Oh, S.-T., et al., "Synthesis and Fungicidal Activities of Polymeric Biocides. I. TBZ-Containing Monomer and Polymers," *J. Applied Polymer Sci.* 52(5):583-589, 1994.

Oh, S.-T., et al., "Synthesis and Biocidal Activities of Polymer. III. Bactericidal Activity of Homopolymer of AcDP and Copolymer of AcD With St," *J. App. Polymer Sci.* 54(6):859-866, 1994.

Panangala, V.S., et al., "Inactivation of rotavirus by new polymeric water disinfectants," *J. Virol. Methods* 66:263-268 (1997).

S.D. Worley, Ph.D. and J.F. Williams, Ph.D., "Disinfection of Water by N-Halamine Biocidal Polymers," *Water Conditioning & Purification*, 96-100 (Jul. 1997).

Shull, K.E., "Experience With Chloramines as Primary Disinfectants," *J. Am. Water Works Assoc.* 73:101-104, 1981.

Sun, G., et al., "A New Cyclic N-Halamine Biocidal Polymer," *Ind. Eng. Chem. Res.* 33:168-170, 1994.

Sun, G., et al., "Preparation of Novel Biocidal N-Halamine Polymers," *J. Bioactive and Compatible Polymers* 10:135-144, 1995.

Sun, G., et al., "Disinfection of Water by N-Halamine Biocidal Polymers," *Ind. Eng. Chem. Res.* 34:4106-4109, 1995.

Sun, G., et al., "Performance of a New Polymeric Water Disinfectant," *J. Am. Water Res. Assoc.* 32(4):793-797, 1996.

Tsao, T.-C., et al., "Novel N-Halamine Disinfectant Compounds," *Biotechnol. Prog.* 7:60-66, 1991.

Vogt, C., "Controlling Trihalomethanes While Attaining Disinfection," *J. Am. Water Works Assoc.* 73:33-40, 1981.

"Water Absorbing Composition Manufacture" (abstract) [online], Jun. 2000 [retrieved Oct. 4, 2001], retrieved from *West, Derwent World Patents Index* Accession No. 2000-530587.

Williams, D.E., et al., "Is Free Halogen Necessary for Disinfection?," *App. and Environ. Microbiology* 54(10):2583-2585, 1988.

Wolfe, R.L., et al., "Inorganic Chloramines as Drinking Water Disinfectants: A Review," *J. Am. Water Works Assoc.* 76:74-88, 1984.

Worley, S.D., et al., "The Stability in Water of a New Chloramine Disinfectant," *Water Resources Bulletin* 19(1):97-100, 1983.

Worley, S.D., et al., "Halamine Water Disinfectants," *CRC Critical Reviews in Environmental Control* 18(2):133-175, 1988.

Worley, S.D., et al., "Biocidal Polymers," *Trip* 4(11):364-370, 1996.

Abrams, I.M., and J.R. Millar, "A History of the Origin and Development of Macroporous Ion-Exchange Resins," *Reactive and Functional Polymers* 35(1):7-22(16), Dec. 1997.

Li, F.-Y., et al., Research on the Preparation of Insoluble Hydantoin Bactericide From Chloromethyl Polystyrene Resin, Fine Chemicals 17(4):220-222, Apr. 2000, Peoples Republic of China (with English translation).

Sherrington, D.C., "Preparation, Structure and Morphology of Polymer Supports," Chemical Communications 21:2275-2286, 1998.

Atobe, I., et al., "Synthesis and Radical Polymerization of Vinyl Monomers Having Oxazolidone Moiety," Journal of Polymer Science: Part A, Polymer Chemistry 31(6):1543-1549, May 1993.

Elrod, D.B., and S.D. Worley, "Synthesis of Novel H-Halamine Biocidal Polymers," Journal of Bioactive and Compatible Polymers 14(3):258-269, May 1999.

Notice of Reasons for Rejection (JP), mailed Jun. 9, 2009, issued in corresponding Japanese Application No. 2004-550178.

Sun, Y., and G. Sun, "Synthesis, Characterization, and Antibacterial Activities of Novel N-Halamine Polymer Beads Prepared by Suspension Copolymerization," Macromolecules 35(23):8909-8912, Oct. 3, 2002.

\* cited by examiner

BIOCIDAL PARTICLES OF METHYLATED POLYSTYRENE

FIELD OF THE INVENTION

The present invention relates to the use of highly crosslinked, porous N-halamine biocidal polymers for inactivating pathogenic microorganisms and viruses in water and air filtration applications, thereby rendering the water and/or air safe for human consumption. The invention also relates to the use of these polymers for inactivating microorganisms such as bacteria, fungi, and yeasts that can cause noxious odors and infections in commercial products, such as disposable diapers, infant swimwear, incontinence pads, bandages, sanitary napkins, pantiliners, sponges, mattress covers, shoe inserts, animal litter, carpets, fabrics, and air filters, thereby rendering the products free of noxious odors and pathogenic organisms under normal use conditions.

BACKGROUND OF THE INVENTION

While a variety of biocidal polymers [e.g., quaternary ammonium salts, phosphonium materials, halogenated sulfonamides, and biguanides (see *Trends Polym. Sci.* 4:364 (1996))] have been synthesized and tested for biocidal activity, a relatively new class of compounds known as N-halamines has been shown to have far superior properties including biocidal efficacy, long-term stability, and rechargeability once the efficacy has been lost. One example of a biocidal N-halamine polymer is poly-1,3-dichloro-5-methyl-5-(4'-vinylphenyl)hydantoin, which is an inexpensive derivative of polystyrene, and which was first described in U.S. Pat. No. 5,490,983, incorporated herein by reference in its entirety. Subsequent disclosures of its biocidal properties for use in disinfecting applications for water filters have recently occurred [see *Ind. Eng. Chem. Res.* 33:168 (1994); *Water Res. Bull.* 32:793 (1996); *Ind. Eng. Chem. Res.* 34:4106 (1995); *J. Virolog. Meth.* 66:263 (1997); *Trends in Polym. Sci.* 4:364 (1996); *Water Cond. & Pur.* 39:96 (1997)]. The polymer is effective against a broad spectrum of pathogens including *Staphylococcus aureus, Pseudomonas aeruginosa, Escherichia coli Candida albicans, Klebsiella terrigena, Legionella pneumophila,* and rotavirus, among others. The polymer causes large log reductions in contact times on the order of a few seconds in water disinfectant applications. Furthermore, the polymer is effective at pH values at least in the range of about 4.5 to about 9.0 and at temperatures at least in the range of about 4° C. to about 37° C., and is capable of action even in water containing heavy chlorine demand caused by bioburden.

The biocidal hydantoin polymer is insoluble in water and organic compounds and will thus not migrate in liquid media. The polymer is stable for long periods of time in dry storage (a shelf life of at least one year at ambient temperature). The polymer can be produced on an industrial scale. Furthermore, all evidence obtained to date suggests that the polymer is non-toxic and non-sensitizing to humans and animals upon contact.

A variety of microorganisms such as certain bacteria, fungi, and yeasts are capable of aiding the decomposition of bodily fluids, such as urine and blood, or in the formation of biofilms, that produce undesirable odors in otherwise useful commercial products. Bacteria such as *Bacterium ammoniagenes* and *Proteus mirabilis* are known to accentuate the decomposition of urea to form noxious ammonia gas through a urease enzyme catalysis mechanism (see for example U.S. Pat. No. 5,992,351). The polymer poly-1,3-dichloro-5-methyl-5-(4'-vinylphenyl)hydantoin has been shown to be effective at inactivating *Proteus mirabilis* and thus minimizing the undesirable odor created by ammonia gas (U.S. patent application Ser. No. 09/685,963, incorporated herein by reference in its entirety). Also, the polymer is insoluble in bodily fluids so as not to migrate to skin surfaces, thus rendering it useful for disposable diapers, incontinence pads, bandages, sanitary napkins, and pantiliners.

However, the preparation of poly-1,3-dichloro-5-methyl-5-(4'-vinylphenyl)hydantoin as uniform particles is tedious, requiring a three-step synthesis and the use of reagents such as potassium cyanide and carbon disulfide, as well as a high-pressure reactor in one of the steps. When fully chlorinated, the polymer binds about 20% by weight chlorine, which causes a noticeable chlorine odor. Thus, new biocidal compounds are desired to be developed having fewer of these disadvantages.

U.S. patent application Ser. No. 09/948,945, incorporated herein by reference in its entirety, describes biocidal beads of highly crosslinked polystyrene having pendant N-halamine groups. In this application, the aforementioned shortcomings in the prior art were addressed. However, other alternatives are desired. The present application fulfills the shortcomings of the prior art and provides further related advantages.

SUMMARY OF THE INVENTION

The present invention relates to a polymer having repeating styrene units that have pendant halogenated and nonhalogenated N-halamine groups linked to the benzene ring of the styrene through a methylene group. The non-halogenated forms are referred to as N-halamine precursors. In one aspect, the present invention relates to methylated polystyrene compounds having pendant N-halamine precursors and to the biocidal methylated polystyrene compounds having N-halamine groups and to the methods for their preparation.

An N-halamine group is a heterocyclic, monocyclic 4 to 7 membered ring, wherein at least 3 members of the ring are carbon, from 1 to 3 members of the ring are nitrogen heteroatom, from 0 to 1 member of the ring is oxygen heteroatom, and wherein 0 to 2 carbon members are carbonyl. At least one ring nitrogen has a chlorine or bromine atom bonded to it. A precursor N-halamine group is the heterocyclic group without any chlorine or bromine atoms on any ring nitrogens. A precursor N-halamine group has a hydrogen, or a hydroxy alkyl group bonded to all ring nitrogens that are not bonded to a linking group. In one embodiment the linking group is a methylene group. The methylene group bonds the N-halamine or N-halamine precursor group to the benzene ring of polystyrene. Representative of N-halamine and N-halamine precursor groups are the halogenated and nonhalogenated hydantoins, imidazolidinones, oxazolidinones, and isocyanurates.

The polymeric compounds of the invention are preferably derived from methylated polystyrene particles. The particles can be used in absorbent articles that have an absorbent core with absorbent material. Methylated polystyrene refers to a polystyrene having a methylene group bonded to the benzene ring of the polystyrene. The methylene group is a linkage to the N-halamine or N-halamine precursor group. A representative methylated polystyrene is poly(p-methyl)styrene. A representative functionalized methylated polystyrene is poly(p-chloromethyl)styrene. In one embodiment of the invention, chloromethylated polystyrene crosslinked with divinylbenzene is used as a starting material for making the compounds of the invention. However, other crosslinking agents may be utilized. Anticipated uses for the biocidal compounds of this invention are for the disinfection of a variety of bacteria-carrying media, including, but not limited to, water, oil, and air. The compounds of the invention can be combined with absorbent materials and incorporated into absorbent products for the disinfection and the prevention of noxious odors caused by the decomposition of organic materials contained in bodily fluids.

A further embodiment of the invention relates to the synthesis of methylated polystyrene having N-halamine precursor groups, and their biocidal derivatives. N-halamine precursors are made biocidal when at least one ring nitrogen is bonded to a halogen. Preferably, the halogen is either a chlorine or bromine atom.

In one embodiment to make the compounds of the invention, porous beads of highly crosslinked functionalized methylated polystyrene reactive toward N-halamine precursors is used as the starting material. The methylated polystyrene is functionalized by placing a halogen, such as a chlorine atom, on the methyl group, making the polystyrene reactive toward a N-halamine or a N-halamine precursor group.

In one embodiment, the invention provides a polystyrene having a N-halamine precursor group bonded to at least some of the benzene rings of the polystyrene by a methylene group.

In another embodiment, the invention provides a polystyrene having a biocidal N-halamine group bonded to at least some of the benzene rings of the polystyrene by a methylene group.

In a further embodiment, the invention provides a method for making a methylated polystyrene having pendant N-halamine precursor groups. The method includes reacting a functionalized methylated polystyrene with an N-halamine precursor and an alkali metal base to produce a methylated polystyrene having pendant N-halamine precursor groups. In one embodiment, the appropriated functionalized methylated polystyrene is reacted with an N-halamine precursor and the base for from about 12 to about 96 hours at a temperature of from about 70° to about 120° C. To make the polystyrene biocidal requires halogenating the methylated polystyrene having pendant N-halamine precursor groups to produce the biocidal methylated polystyrene having pendant N-halamine groups.

An alternate embodiment for making a methylated polystyrene having pendant N-halamine precursor groups includes reacting an N-halamine precursor with an alkali metal base to produce an alkali metal salt of the N-halamine precursor. In one embodiment, the N-halamine precursor is reacted with the alkali metal base for from about 15 minutes to about 2 hours at a temperature of from about 25° to about 100° C. The method includes reacting the alkali metal salt of the N-halamine precursor with a functionalized methylated polystyrene to produce a methylated polystyrene having pendant N-halamine precursor groups. In one embodiment, the appropriated functionalized methylated polystyrene is reacted with the N-halamine precursor salt for from about 4 to about 96 hours at a temperature of from about 70° to about 120° C. Either method of making a methylated polystyrene having pendant N-halamine precursor groups is used to make the biocidal derivative, and involves halogenating the methylated polystyrene having pendant N-halamine precursor groups to produce the biocidal methylated polystyrene having pendant N-halamine groups.

One embodiment of the invention relates to the use of the biocidal polymeric compounds in filters for the disinfection of water and air.

One embodiment of the invention relates to the disinfection and control of odor in bodily fluids in applications such as disposable diapers, infant swimwear, incontinence pads, bandages, sanitary napkins, pantiliners, and the like.

Biocidal compounds made according to the present invention using chloromethylated polystyrene beads as a starting material require fewer steps to synthesize and produce less chlorine outgassing than the previously produced N-halamine polymer of U.S. Pat. No. 5,490,983 to Worley et al., while maintaining a reasonable biocidal efficacy. Chloromethylated polystyrene beads have been utilized in the past to prepare ion-exchange resins and weakly biocidal polyquaternary ammonium salts (U.S. Pat. No. 4,349,646 and U.S. Pat. No. 4,826,924), but have not been functionalized with potent biocidal N-halamine moieties.

DETAILED DESCRIPTION OF THE PREFERRED EMBODIMENT

The present invention may be understood more readily by reference to the following detailed description of specific embodiments and the examples included therein.

One embodiment of the invention provides a polymer having a repeating unit, wherein the repeating unit has the structure:

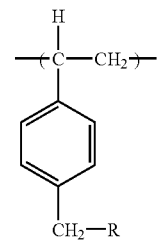

The moieties R of the repeating unit are selected from among the following N-halamine precursors when X is hydrogen, or N-halamines when X is chlorine or bromine:

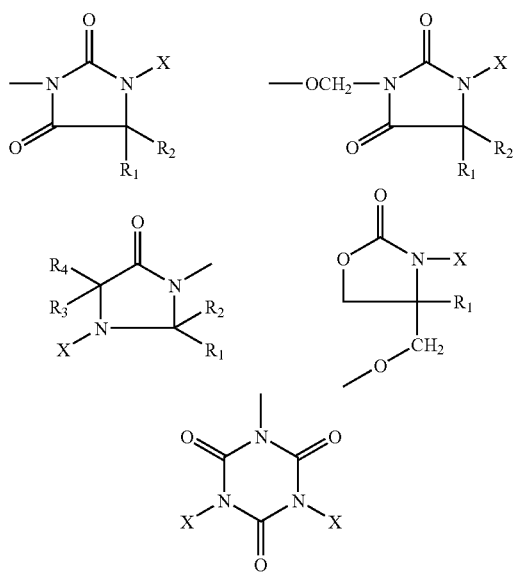

wherein $R_1$, $R_2$, $R_3$, and $R_4$ are independently selected from $C_1$-$C_4$ alkyl, phenyl, or aryl; X is hydrogen, chlorine, or bromine, at least one of which must be chlorine or bromine when the compound is a biocidal N-halamine, X is not chlorine or bromine for N-halamine precursors. "Independently selected" encompasses all the combinations of the one or more $R_n$ groups possible with the moieties selected from $C_1$-$C_4$ alkyl, phenyl and aryl. Thus, the $R_n$ groups can all be the same group or can all different groups or any other combination. The repeating unit appears consecutively if the polymeric compound is a homopolymer, or alternatively with one or more different repeating units if the polymeric compound is a copolymer.

In one aspect of the invention, methylated polystyrene having pendant N-halamine precursor groups and biocidal methylated polystyrene having pendent N-halamine groups are provided, wherein the N-halamine and N-halamine precursor groups are either a halogenated or nonhalogenated hydantoin, imidazolidinone, oxazolidinone, or isocyanurate.

In one embodiment, the invention provides a methylated polystyrene having pendant N-halamine precursor groups. The methylated polystyrene is derived from highly crosslinked chloromethylated polystyrene. The methylated polystyrene having pendant N-halamine groups is biocidal by virtue of the halogen bonded to a nitrogen of the heterocyclic moiety. The methylated polystyrenes of the invention are highly crosslinked and therefore are insoluble polymer beads. In one embodiment, the methylated polystyrene having pendant N-halamine groups is a biocidal polymer bead.

The biocidal polymer beads can be employed in a filter for water, cutting oils, or air disinfection. The biocidal polymer beads can be mixed with an absorbent material. Suitable absorbent materials include the materials in disposable diapers, including natural and synthetic fibers. Among the natural fibers are cellulose fibers, most commonly derived from wood pulp. Synthetic fibers include polyolefins, among others. Polyolefins include polypropylene and polyethylene. Superabsorbent polymers may be combined with the biocidal polymers of the present invention. In absorbent articles, the biocidal polymer of the invention can make up from about 0.1 to about 5.0 weight percent, more preferably a weight percent of about 1.0 for applications involving bodily fluids, including disposable diapers, infant swimwear, incontinence pads, bandages, sanitary napkins, pantiliners, mattress covers, shoe inserts, sponges, and animal litter. The weight percent is based on the combined weight of the polymer and any absorbent core components, such as wood pulp, any synthetic or natural fibers, cellulose fibers, polyolefin fibers, superabsorbent polymers, and the like. For air filters, coatings, or simple embedment of the biocidal polymer into available filter materials, a weight percent of from about 0.1 to about 2.0, more preferably a weight percent from about 0.5 to about 1.0 is considered suitable. The weight percent is based on the combined weight of polymer and any filler materials.

The biocidal polymer beads of the invention will inactivate pathogenic microorganisms and viruses contained in water or air media that comes in contact with the beads. In some applications, it is desirable to allow the media to flow through and contact the beads. The biocidal beads prevent or minimize noxious odors. It is believed the biocidal beads inactivate the microorganisms that enhance the decomposition of organic matter in bodily fluids to ammonia or other noxious materials. When biocidal, the beads will prevent or minimize noxious odors in air filters by inactivation of microorganisms including those that cause mildew and molds, as well as those from any liquid or aerosol which might contact the surface of the beads. The mechanism of action of the biocidal polymer is believed to be a result of surface contact of the microorganism with chlorine or bromine atoms covalently bound to the N-halamine groups of the polymer. The chlorine or bromine atoms are transferred to the cells of the microorganisms where they cause inactivation through a mechanism not completely understood, but probably involving oxidation of essential groups contained within the enzymes comprising the organisms.

A wide variety of cartridge filtration devices can be used that incorporate the biocidal polymer beads, including very large units in small water treatment plants and in the air-handling systems of large aircraft, hotels, and convention centers, and small filters as might be employed in household carafes and for faucets and portable devices for backpacking and military field use. A broad variety of absorbent and filler materials can be used in combination with the biocidal polymer to aid in preventing noxious odors. Absorbent materials are able to hold fluids, aerosol particles, and solid contaminants for sufficient periods of time such that the biocidal polymer beads can make contact with the odor-causing microorganisms. Absorbent materials include, but are not limited to, swellable clays, zeolites, alumina, silica, cellulose, wood pulp, superabsorbent polymers and fibers, including polyolefin fibers, such as polypropylene fibers and polyethylene fibers. The absorbent material can contain further adjuvants such as deodorants, fragrances, pigments, dyes, and mixtures of these for cosmetic purposes. The biocidal polymer beads can be used within the absorbent cores of diapers, incontinence products, infant swimwear, pantiliners, sanitary napkins, and the like.

A marked advantage of the biocidal polymer beads of this invention over prior odor-controlling technology is that the beads of the invention are much more effective biocides against pathogenic microorganisms, such as *S. aureus* and *P. aeruginosa*, than are the commercial biocides, such as the quaternary ammonium salts. The biocidal polymer beads can serve a dual function: inactivation of odor-causing microorganisms and inactivation of disease-causing pathogens. For this reason, the biocidal polymer beads will have widespread use in medical settings.

It should be understood that the practice of this invention applies to odors generated by both human and animal fluids as well as to airborne and waterborne organisms.

In another aspect, the present invention provides methods for making methylated polystyrene having pendant N-halamine precursor groups and methylated polystyrene having pendent N-halamine groups. As an initial matter, a methylated polystyrene is obtained that has been functionalized to react toward an N-halamine precursor or an N-halamine group. In one embodiment, the methylated polystyrene is functionalized by bonding a chlorine atom to the methylene group. One representative functionalized methylated polystyrene is poly(p-chloromethyl)styrene. Crosslinked poly(chloromethyl)styrene is available from commercial vendors ranging up in size from very small microparticle sizes.

Generally, chemical reactions proceed best when all reactants are dissolved in a solvent that ensures maximum contact of the reactants. It was unexpected that the heterogeneous reaction of the highly crosslinked chloromethylated polystyrene beads, which were insoluble in dimethylformamide (DMF), would proceed well in DMF when simply mixed with N-halamine precursor compounds. However, the reactions carried out in heterogeneous phases proved to provide adequate reaction of N-halamine precursors to the functionalized methylated polystyrene beads. The biocidal polymer beads can be made in a variety of particle sizes dependent upon the particle size of the starting highly crosslinked chloromethylated polystyrene. Another advantage of the highly crosslinked chloromethylated polystyrene is that the beads are porous allowing efficient heterogeneous reactions to be performed. Nonporous beads could be used also with concomitant lower biocidal efficacy. Ideally, for the applications described herein, the particle size of the biocidal polymer bead is preferably in the range of from about 100 to about 1500 µm, more preferably in the range of from about 200 to about 800 µm. Particle sizes within these ranges provide adequate flow characteristics for microbiologically contaminated fluids and lessen the risk of exposure of the respiratory systems of workers to fine aerosolized particles. These two factors provide a marked improvement over the powder versions of poly-1,3-dichloro-5-methyl-5-(4'-vinylphenyl)hydantoin or poly-1,3-dibromo-5-methyl-5-(4'-vinylphenyl) hydantoin disclosed in U.S. Pat. No. 5,490,983 and use for odor control as described in U.S. patent application Ser. No. 09/685,963. Preferably, for the applications contemplated herein, the biocidal polymer beads should have pore sizes in the range of from about 10 to about 100 nm, more preferably, in the range of from about 30 to about 70 nm. The porous structure is advantageous in the synthetic reaction step because the highly crosslinked beads are insoluble in organic solvents and water. The degree of crosslinking of the starting chloromethylated polystyrene should be in the range of from about 3 to about 10 weight percent to ensure hardness and lack of solubility. In one embodiment, the degree of crosslinking is from about 5 to about 8 weight percent. There are many types of highly crosslinked, porous chloromethylated polystyrene beads that can be used in the synthetic reaction step of this invention. Providers of crosslinked chloromethylated polystyrene beads include the Suqing Group (Jiangyin, Jiangsu, PRC) and the Purolite Company (Philadelphia, Pa.).

Representative methods of making a methylated polystyrene having pendant N-halamine precursors are as follows. In one embodiment, clean, highly crosslinked porous chloromethylated polystyrene beads are suspended in a medium, such as DMF. The chloromethylated polystyrene beads are reacted with an N-halamine precursor, such as 5,5-dimethylhydantoin, in the presence of an alkali metal carbonate, such as potassium carbonate, at a temperature from about 70° to about 120° C., preferably about 95° C., for about 12 to about 96 hours to yield the methylated polystyrene having pendant N-halamine precursor groups. The time for this reaction is typically 72 hours when an alkali metal carbonate is employed.

In an alternate embodiment, the alkali metal salt of the N-halamine precursor is prepared first by reacting an N-halamine precursor with an alkali metal base for from about 15 minutes to about two hours at a temperature of from about 25° to about 100° C. The alkali metal base is preferably a carbonate, a hydroxide, or a hydride, and includes an alkali metal chosen from sodium or potassium. The reaction time between the N-halamine precursor and chloromethylated polystyrene is reduced if the alkali metal salt of the N-halamine precursor is prepared first. The salt is then used in the subsequent reaction between the alkali metal salt of the N-halamine precursor with the chloromethylated polystyrene to yield the methylated polystyrene having pendant N-halamine precursor groups. The time and temperature for this subsequent reaction is from about 4 to about 96 hours at a temperature of from about 70° to about 120° C., but typically is about 12 hours or less. Thus, the overall preparation time can be reduced by employing the latter two-step reaction method.

The isolated product beads made through either method are washed in boiling water for purification purposes. After having made the methylated polystyrene bead having pendant N-halamine precursor groups, an aqueous suspension of the bead is chlorinated or brominated to render the bead biocidal. Halogenation is accomplished by exposing the bead to a source of free chlorine (e.g., gaseous chlorine, sodium hypochlorite, calcium hypochlorite, sodium dichloroisocyanurate) or free bromine (e.g., liquid bromine, sodium bromide/potassium peroxymonosulfate) in aqueous base. If chlorine gas is used, the reactor is preferably chilled to about 10° C. to prevent undesirable side reactions. Ambient temperature can be employed for the other noted sources of free halogen, and the reactions can be carried out in a reactor or in situ in a cartridge filter packed with the unhalogenated precursor. Using these methods, typical loadings of about 6-7% by weight chlorine and about 8-9% by weight bromine on the beads are generally obtained.

The present invention is more particularly described in the following examples which are intended as illustrative only since numerous modifications and variations therein will be apparent to those skilled in the art.

EXAMPLES

Example 1

A Representative Preparation of Chlorinated Methylated Polystyrene Hydantoin Beads Porous beads of 5.6% crosslinked chloromethylated polystyrene (containing 20.85% by weight chlorine) obtained from Suqing Group (Jiangyin, Jiangsu, PRC) having particle sizes in the range 180 to 425 µm, but undetermined pore sizes, were cleaned by soaking them in acetone (400 mg/mL) for 30 minutes at 25° C. and then by passing 3 portions of acetone (0.5 mL per g) through them in a filter funnel. Following drying to constant weight under vacuum at 50° C., 20.3 g (about 0.12 mole of active chlorine) of the beads were suspended in 150 mL of anhydrous DMF in a 250 mL flask fitted with a condenser. Then 16.5 g of anhydrous potassium carbonate (0.12 mole) and 15.4 g (0.12 mole) of 5,5-dimethylhydantoin were added, and the mixture was stirred for 72 hours at 95° C. After cooling the mixture to 25° C., suction filtration was used to isolate the beads. The beads were then soaked in 500 mL of boiling water for 15 minutes and subsequently washed with three 100 mL portions of boiling water. Then the beads were dried under vacuum at 85° C. to constant weight (27.2 grams or 34.0% add-on weight). An infrared spectrum of a small sample of the beads (crushed to a powder) in a KBr pellet exhibited prominent bands at 1715 and 1776 $cm^{-1}$, which demonstrated the presence of the hydantoin functional group (the two expected carbonyl stretching bands).

Then 10.0 g of the porous beads having hydantoin functional groups as described above were suspended in a flask containing 50 mL of 5.25% sodium hypochlorite and 50 mL of water, and the pH was adjusted to 7.5 by the addition of 2 N acetic acid. The mixture was stirred for 45 minutes at 25° C., filtered, and washed with three 100 mL portions of water at 25° C. The thus chlorinated beads were dried under vacuum at 50° C. until their weight became constant. A sodium thiosulfate/iodometric titration indicated that the chlorine loading of the dried beads was 6.23% by weight. An infrared spectrum of a small sample of the beads (crushed to a powder) in a KBr pellet exhibited prominent bands at 1726 and 1790 $cm^{-1}$ as expected for a monochlorinated hydantoin functional group.

Example 2

An Alternative Representative Preparation of Chlorinated Methylated Polystyrene Hydantoin Beads The potassium salt of 5,5-dimethylhydantoin was prepared by reacting 25.6 grams (0.2 mole) of 5,5-dimethylhydantoin with 11.2 grams (0.2 mole) of potassium hydroxide in 100 mL of boiling ethanol with stirring. The ethanol and product water were removed under vacuum to obtain the white salt. The salt was added to 200 mL of anhydrous DMF and heated to 95° C. until all of the salt dissolved. Then 8.12 grams (about 0.048 mole of active chlorine) cleaned chloromethylated polystyrene beads were added and the mixture was heated with stirring at about 100° C. for 12 hours. The unreacted potassium salt of the hydantoin and the DMF were recycled for further use, and the beads functionalized with hydantoin groups were washed and dried under vacuum at 85° C. until constant weight as in Example 1. The weight of the beads prepared in this manner was 11.0 grams (35.5% by weight add-on). Chlorination of the beads as in Example 1 produced a chlorine loading of 6.3% by weight. This alternate method of preparing the chlorinated beads would appear to be superior to that in Example 1 as the reaction time for functionalization with the hydantoin moiety is reduced considerably (from 72 to 12 hours).

Example 3

Representative Preparation of Brominated Methylated Polystyrene Hydantoin Beads Methylated polystyrene hydantoin beads (5.0 grams) prepared as described in Example 1 were suspended in a solution containing 40 mL of 10% sodium hypobromite and 40 mL of water. The pH was adjusted to 7.0 using 2 N acetic acid. The mixture was stirred for 1 hour at 25° C. The brominated beads were removed by filtration, washed with three 100 mL portions of water, and dried under vacuum until constant weight was obtained. The bromine content determined by sodium thiosulfate/iodometric titration was 8.2% by weight. An infrared spectrum of a small sample of the beads (crushed to a powder) in a KBr pellet exhibited prominent bands at 1714 and 1776 cm$^{-1}$ consistent with the presence of a monobrominated hydantoin functional group.

Example 4

Representative Preparation of Chlorinated Methylated Polystyrene Hydroxymethylhydantoin Beads Porous beads of 5.6% crosslinked chloromethylated polystyrene (containing 20.85% by weight chlorine) obtained from Suqing Group (Jiangyin, Jiangsu, PRC) having particle sizes in the range 180 to 425 µm, but undetermined pore sizes, were cleaned as described in Example 1. Following drying to constant weight under vacuum at 50° C., 10.57 g (about 0.062 mole of active chlorine) of the beads were suspended in 150 mL of anhydrous DMF in a 250 mL flask fitted with a condenser. Then 10.7 g of anhydrous potassium carbonate (0.078 mole) and 12.3 g (0.078 mole) of 1-hydroxymethyl-5,5-dimethylhydantoin were added, and the mixture was stirred for 48 hours at 100° C. After cooling the mixture to 25° C., suction filtration was used to isolate the beads functionalized with hydantoin groups. The beads were then washed with three 100 mL portions of water, soaked in 250 mL of boiling water for 15 minutes, and subsequently washed with two 100 mL portions of water. Then the beads were dried under vacuum at 85° C. to constant weight (13.98 grams or 32.3% add-on weight). An infrared spectrum of a small sample of the beads (crushed to a powder) in a KBr pellet exhibited prominent bands at 1715 and 1777 cm$^{-1}$ which demonstrated the presence of the hydantoin functional group (the two expected carbonyl stretching bands).

Then 5.0 g of the porous beads functionalized with hydantoin groups as described above were suspended in a flask containing 40 mL of 5.25% sodium hypochlorite and mL of water, and the pH was adjusted to 7.5 by the addition of 2 N acetic acid. The mixture was stirred for 1 hour at 25° C., filtered, and washed with three 100 mL portions of water at 25° C. The thus chlorinated beads were dried under vacuum at 50° C. until their weight became constant. A sodium thiosulfate/iodometric titration indicated that the chlorine loading of the dried beads was 6.83% by weight. An infrared spectrum of a small sample of the beads (crushed to a powder) in a KBr pellet exhibited prominent bands at 1728 and 1792 cm$^{-1}$ as expected for a monochlorinated hyroxymethylhydantoin functional group.

Example 5

Representative Preparation of Chlorinated Methylated Polystyrene Imidazolidinone Beads To a 250 mL flask were added 2.84 g (0.02 mole) of 2,2,5,5-tetramethylimidazolidin-4-one (TMIO) prepared as described in Tsao, et al., *Biotech. Prog.* 7:60 (1991); 0.49 g (0.02 mole) of sodium hydride; and 100 mL of anhydrous DMF. After stirring the mixture for 2 hours at 25° C., 6.0 g (0.035 mole of active chlorine) of chloromethylated polystyrene beads were added. The mixture was stirred at 95° C. for 48 hours, cooled, filtered, and the beads functionalized with imidazolidinone groups were washed with two 100 mL portions of water and then held in boiling water for 15 minutes. After filtration, the beads were again washed with two 100 mL portions of water and then dried under vacuum at 75° C. until constant weight (6.65 g) was obtained. The percent by weight add-on was 10.8%. This add-on percentage was lower than for the other beads described in previous examples. An infrared spectrum of a small sample of the beads (crushed to a powder) in a KBr pellet exhibited prominent bands at 1613 and 1696 cm$^{-1}$ which demonstrated the presence of the imidazolidinone functional group most probably bonded to the polymer beads at the amide nitrogen of the heterocyclic moiety.

Then 3.4 g of the beads functionalized with imidazolidinone groups were soaked in 20 mL of 5.25% sodium hypochlorite and 20 mL water at a pH of 7.5 (adjusted by addition of 4 N acetic acid) at 25° C. for 1 hour. After filtration and washing with three 100 mL portions of water, the beads were dried to constant weight under vacuum at 50° C. A sodium thiosulfate/iodometric titration indicated that the chlorine loading of the dried beads was 2.85% by weight. An infrared spectrum of a small sample of the beads (crushed to a powder) in a KBr pellet exhibited prominent bands at 1609 and 1717 cm$^{-1}$ indicative of a rather low chlorine loading.

Example 6

Stability of Chlorinated Methylated Polystyrene Hydantoin Beads

Chlorinated methylated polystyrene hydantoin beads prepared as described in Example 1 (5.0 g) were dried under vacuum at about 50° C. until constant weight was obtained. These beads were stored in a capped brown bottle. Periodically over 90 days samples were removed for analytical determination of chlorine content using a sodium thiosulfate/iodometric titration procedure. The data are shown in Table 1.

TABLE 1

Stability of Chlorinated Methylated Polystyrene Hydantoin Beads

| Time (days) | Weight Percent Cl | % Decrease in Cl |
| --- | --- | --- |
| 0 | 6.30 | — |
| 14 | 6.13 | 2.7 |
| 28 | 5.90 | 6.3 |
| 60 | 5.68 | 9.8 |
| 96 | 5.49 | 12.9 |

It can be concluded that the chlorine stability of the beads is quite good and that the beads remain biocidal for more than 96 days.

Example 7

Biocidal Efficacy Testing of Representative Biocidal Polymer Beads

The beads as prepared in Examples 1-4 were tested for biocidal activity against two pathogens contained in water. In the tests, about 3.3-3.4 g of biocidal halogenated beads were packed into glass columns having inside diameter 1.3 cm to a length of about 7.6 cm; the empty bed volumes of the beads ranged from 2.9 to 4.4 mL. Identical sample columns of unhalogenated beads were prepared to be used as controls. After washing the columns with demand-free water until less than 0.2 mg/L of free chlorine or 0.5 mg/L of free bromine could be detected in the effluent, an aqueous solution of 50 mL of pH 7.0 phosphate-buffered, demand-free water containing $3.6$-$5.5 \times 10^6$ CFU (colony forming units)/mL of the Gram positive bacterium Staphylococcus aureus (ATCC 6538) or $4.9$-$6.8 \times 10^6$ CFU (colony forming units)/mL of the Gram negative bacterium O157:H7 Escherichia coli (ATCC 43895) was pumped through the column at a measured flow rate of about 2.9 to 4.4 mL/second, so as to achieve a contact time of about 1 second in the column per pass. A 25 µL aliquot of the effluent was quenched with 0.02 N sodium thiosulfate before plating, and the remainder of the 50 mL inoculum was immediately recycled through the column. This process was repeated 4 more times, i.e., 6 passes through the column. The contact times necessary to achieve complete inactivation (6.6-6.8 logs/mL) of the two bacteria were 1-2 seconds for the chlorinated methylated polystyrene hydantoin beads and less than or equal to 1 second for the brominated methylated polystyrene hydantoin beads and the chlorinated methylated polystyrene hydroxymethylhydantoin beads. For the chlorinated methylated polystyrene imidazolidinone beads, longer contact times (2-3 seconds for a 6.6 log/mL reduction of S. aureus and about 6 seconds for about a 4.0 log/mL reduction of E. coli) were required. The control columns containing unhalogenated beads gave no reduction of either bacterium in a contact time of greater than 60 seconds when the same concentrations of the inoculums were employed, indicating that the bacteria in the halogenated columns were inactivated, rather than just removed by filtration.

The results in this example indicate that the beads prepared as described in Examples 1-5 possess considerable efficacy against bacterial pathogens in aqueous solution and are excellent materials for use in the disinfection of water, in particular for recirculated water.

Example 8

Odor Control

Beads prepared as described in Example 1 containing chlorine loadings of about 6.2% by weight were evaluated as to their efficacies in controlling ammonia generation through inactivation of Proteus mirabilis.

Blends of 5-10 mg of chlorinated beads and 1.0 g of wood pulp (0.5 or 1.0% by weight beads) were prepared by mixing with 200 mL of distilled water in a blender (Hamilton Beach 7 Blend Master Model 57100, whip setting). Following vacuum filtration, which produced wood-pulp pads, and drying in air at 25° C., the samples were placed in Petri dishes.

An inoculum known to provide a high level of odor was formulated. The formulation included 9 mL of a mixture of 25 mL of pooled human female urine and 1.25 g of urea and 1 mL of an aqueous suspension of about $1.3 \times 10^8$ CFU/mL of Proteus mirabilis.

Each sample, including a control of wood pulp with non-halogenated polymer, was inoculated with 1 mL of the formulation described above, and the Petri dishes were sealed with parafilm and incubated at 37° C. for 24 hours. The samples were then measured for ammonia production using Drager tubes (Fisher Scientific, Pittsburgh, Pa., and Lab Safety Supply, Janesville, Wis.) capable of detection in the range 0.25 to 30 mg/L. The control sample registered an ammonia concentration greater than 30 mg/L in a contact time interval of 2 to 4 hours, while the chlorinated samples (0.5 and 1.0% bead/wood pulp mixtures) registered ammonia concentrations of only 1.5 to 2.0 mg/L after 4 hours contact and only about 2.0 mg/L after 24 hours contact.

It can be concluded that the porous chlorinated beads are highly effective at preventing ammonia generation and hence noxious odor even at very low blends with an absorbent material like wood pulp.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A biocidal methylated polystyrene having pendant hydantoin groups, each hydantoin group being linked from a first nitrogen atom via a methylene group pendant from a carbon atom of each benzene ring of the polystyrene to which each hydantoin group is attached, wherein said biocidal methylated polystyrene is prepared from a porous methylated polystyrene that is at least 3% crosslinked, and a chlorine or bromine atom is bonded to a second nitrogen atom of a hydantoin group.

2. The biocidal methylated polystyrene of claim 1, wherein the polystyrene is crosslinked with divinylbenzene.

3. The biocidal methylated polystyrene of claim 1, wherein the polystyrene is from about 3 to about 10 percent crosslinked.

4. The biocidal methylated polystyrene of claim 1, wherein the polystyrene is from about 5 to about 8 percent crosslinked.

5. The biocidal methylated polystyrene of claim 1, wherein the methylated polystyrene is a chloromethylated polystyrene.

6. The biocidal methylated polystyrene of claim 1, wherein the biocidal methylated polystyrene is chlorinated to at least 6% Cl in an aqueous base.

7. A polymer having a repeating unit, said unit having the formula:

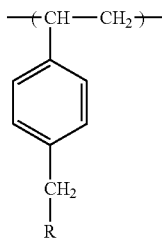

wherein R comprises the hydantoin group:

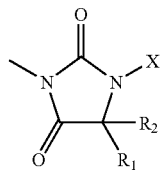

wherein $R_1$ and $R_2$ are independently selected from $C_1$-$C_4$ alkyl, phenyl, and aryl; and X is chlorine or bromine, and wherein said polymer is prepared from a porous methylated polystyrene that is at least 3% crosslinked.

8. The polymer of claim 7, it wherein $R_1$ and $R_2$ are methyl.

9. The polymer of claim 7, wherein the methylated polystyrene is a chloromethylated polystyrene.

10. A biocidal polystyrene having a hydantoin group bonded from a first nitrogen atom to at least some of the benzene rings of the polystyrene via a methylene group pendant on a carbon atom of each benzene ring to which a hydantoin group is attached, wherein said polystyrene is prepared from a porous methylated polystyrene that is at least 3% crosslinked, and a chlorine or bromine atom is bonded to a second nitrogen atom of a hydantoin group.

11. The biocidal polystyrene of claim 10, wherein the methylated polystyrene is a chloromethylated polystyrene.

12. The biocidal polystyrene of claim 10, wherein the biocidal methylated polystyrene is chlorinated to at least 6% Cl in an aqueous base.

13. A bead comprising a crosslinked polystyrene polymer having a repeating unit having the formula:

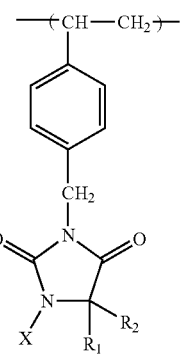

wherein $R_1$ and $R_2$ are independently selected from $C_1$-$C_4$ alkyl, phenyl, and aryl X is chlorine or bromine, and wherein said bead is prepared from a porous methylated polystyrene that is at least 3% crosslinked.

14. The bead of claim 13, wherein $R_1$ and $R_2$ are methyl.

15. The bead of claim 13, wherein X is chlorine.

16. The bead of claim 13, wherein X is bromine.

17. The bead of claim 13, wherein $R_1$ and $R_2$ are methyl and X is chlorine.

18. The bead of claim 13, wherein $R_1$ and $R_2$ are methyl and X is bromine.

19. The bead of claim 13, wherein the methylated polystyrene is a chloromethylated polystyrene.

20. The bead of claim 13, wherein the bead is chlorinated to at least 6% Cl in an aqueous base.

21. The polymer of claim 7, wherein the polymer is chlorinated to at least 6% Cl in an aqueous base.

* * * * *